(12) United States Patent
Skeen

(10) Patent No.: US 6,338,825 B1
(45) Date of Patent: Jan. 15, 2002

(54) PIPETTE TIP HAVING PLURAL CHANNELS AND A TITRATION KIT THEREFOR

(76) Inventor: Jay Skeen, 15034 Hat Creek Rd., Poway, CA (US) 92064

( * ) Notice: Subject to any disclaimer, the term of this patent is extended or adjusted under 35 U.S.C. 154(b) by 0 days.

(21) Appl. No.: 09/385,519

(22) Filed: Aug. 30, 1999

(51) Int. Cl.[7] .................................................. B01L 3/02
(52) U.S. Cl. ................. 422/100; 73/864.01; 73/864.17; 422/61
(58) Field of Search ..................... 422/100, 61; 436/54, 436/180; 73/864.01, 864.17

(56) References Cited

U.S. PATENT DOCUMENTS

| | | | |
|---|---|---|---|
| 3,991,616 A | * | 11/1976 | Stahli |
| 4,469,151 A | * | 9/1984 | Wilson et al. |
| 4,548,245 A | * | 10/1985 | Crandell et al. |
| 5,000,921 A | * | 3/1991 | Hanaway et al. |
| 5,343,909 A | * | 9/1994 | Goodman |
| 5,844,686 A | * | 12/1998 | Treptow et al. |
| 6,074,609 A | * | 6/2000 | Gavin et al. |

OTHER PUBLICATIONS

Fisher Scientific Catalog '88, p. 885, 1988.*

* cited by examiner

Primary Examiner—Jan Ludlow
(74) Attorney, Agent, or Firm—Cowan, Liebowitz & Latman, P.C.; William H. Dippert

(57) ABSTRACT

A pipette tip having at least two separate dispensing channels for dispensing liquid simultaneously into a corresponding number of micro titration wells or other container. The tip has a tubular body with one open end for mounting on a pipette. At the other end of the body, at least two spaced legs extend away from the body, each having a central channel communicating with the tip interior and an end opening. The tips are stored in a rack having an alignment arrangement, such as a ridge on each tip cooperating with a notch in the rack, to assure that all tips are aligned the same. The leg channels can be configured so that different amounts of liquid are dispensed into different micro titration wells in a predetermined pattern. The tip may also be used to transfer liquid from one micro titration plate to another, or any suitable container.

10 Claims, 1 Drawing Sheet

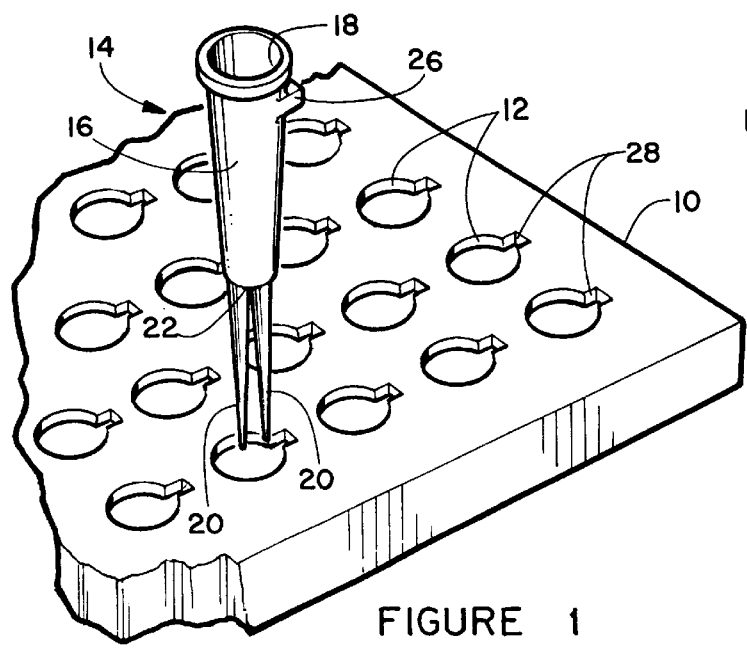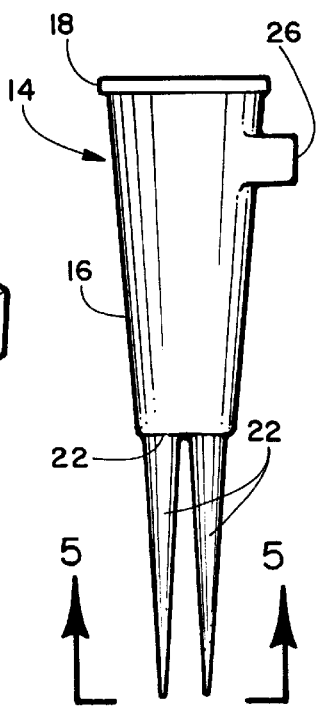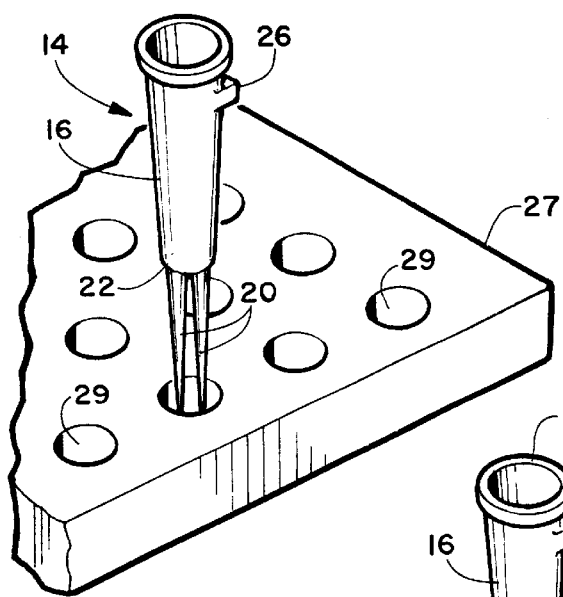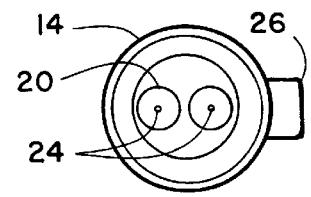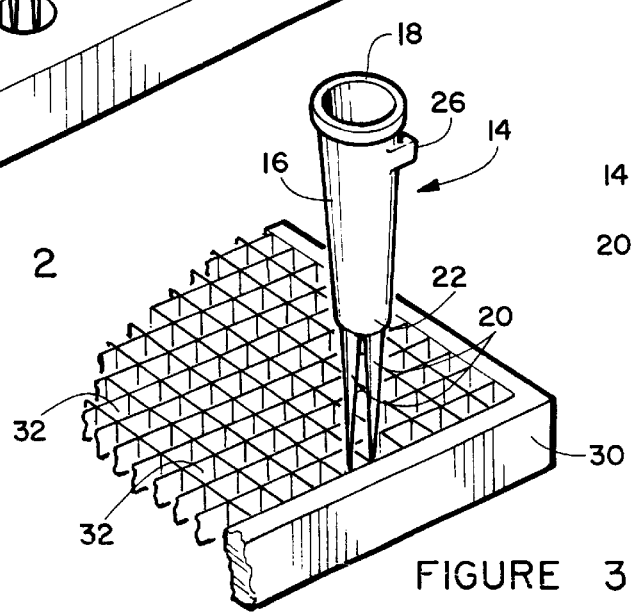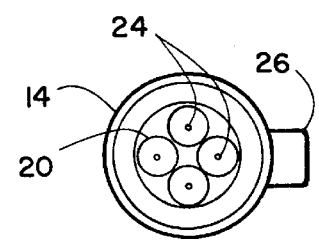

PIPETTE TIP HAVING PLURAL CHANNELS AND A TITRATION KIT THEREFOR

FIELD OF THE INVENTION

This invention relates to disposable tips for pipettes for transferring a volume of liquid from a supply container to microtiter plate wells or other containers.

BACKGROUND OF THE INVENTION

Pipettes have long been used for transferring precise amounts of liquid from one container to another. A narrow end of a tubular pipette is filed with the desired volume of liquid, by air displacement, positive displacement or capillary action, then the volume is dispensed by positive or air displacement. Generally, a disposable plastic pipette tip is mounted on the pipette end to avoid having to clean or sterilize the pipette. The tipped pipette can be moved between the filling and dispensing stations manually or by automated equipment.

In automated pipettors, the pipette is moved to a multi-tip supply rack, the pipette end is inserted into a pipette tip which is held onto the pipette by friction. The tipped pipette is then moved to a supply well and inserted below a liquid level in the supply well. The pipette tip is filled with a precise quantity of liquid and then is moved to a well in a titer plate and dispensed. The sequence is repeated for each of the titer plate wells.

While this operation is quite rapid, increases in rapidity of performing these steps can be very beneficial where a very large number of tests are being performed, as in large scale high throughput screening, testing of potential drugs, such as receptor binding assays, in molecular biology, such as DNA sequencing and DNA fingerprinting, in immunology such as forensic blood typing and other related fields.

Devices having a number of parallel pipettes have been developed to allow simultaneous operation of the pipettes. Typical of these are the devices described by Suovaniemi et al. in U.S. Pat. No. 4,215,092 and Goodman in U.S. Pat. No. 5,343,909. While generally effective, these devices use separate pipettes and operated simultaneously, so that precise calibration filling of all tips with the desired liquid volume is more difficult. All pipettes will be filled with the same quantity of liquid, so that varying liquid quantity in a predetermined pattern among the wells across a plate is difficult. Further, the devices are complex and expensive, using a separate pipette for each well.

Thus, there is a continuing need for improved pipette apparatus that can rapidly dispense a precise volume of liquid to very small wells in a microtiter plate or the like, is simple in construction and operation, is adaptable to existing liquid handling equipment, is inexpensive, and can dispense different volumes of liquid into different wells in a predetermined pattern across a microtiter plate and can be easily and conveniently automated.

SUMMARY OF THE INVENTION

The above-noted problems, and others, are overcome in accordance with this invention by a pipette tip comprising a tubular body portion having a first end for placement over an end of a pipette with the interior of the tip first end configured to fit over the end of a pipette and be retained thereon. At least two spaced, approximately parallel, elongated legs are connected at a leg proximal end to a second end of the tubular body portion. Each leg has a coaxial channel therethrough, communicating at the leg proximal end with said tip body portion interior and having an open distal end.

The plural legs are configured to fit together into a reagent supply well of predetermined cross sectional area and to align with and individually fit within closely spaced titer wells, the titer wells having cross sectional areas less than that of the supply well. Thus, a single pipette tip mounted on a single pipette can simultaneously draw a liquid into each of the pipette tip channels from a single supply well, then simultaneously dispense the liquid from each channel into a different titer well, greatly speeding up dispensing without requiring multiple pipettes and complex handling apparatus. The system may also be used to transfer liquids among different similarly sized wells, such as between different small titer wells.

A storage rack is provided to support a plurality of pipette tips prior to use. Cooperating alignment means are provided on each pipette tip and the storage rack to assure that each tip will mount on each pipette in precisely the same predetermined alignment. This is critical, since when the pipette tip is filled with liquid and brought to the titer plate, the two or more channels must align with the pattern of wells in the titer plate to assure that the liquid is properly dispensed. In one preferred embodiment, a ridge extends from a side of the pipette tip and fits in a corresponding notch in the side of the storage rack opening holding the tip.

In many cases, all of the channel open ends will have the same diameter so that the same quantity of liquid will be dispensed into each titer well in the selected pattern. However, in one particularly preferred embodiment the tip openings for the different channels will be different. For example, with four channels of different outlet diameters the diameters may vary in cross sectional area to provide one quantity in the first well, two quantities in the second well, three quantities in the third well and four quantities in the fourth well. Similarly, the quantities dispensed by the four channels could vary to provide a variety of different quantities in different wells. Thus with drug screening tests and the like, the effectiveness of different ratios of drug to test material can be easily and automatically varied. Clearly, the tip alignment means discussed above is of critical importance with this embodiment, so that the correct amounts of test liquid will always be dispensed into the correct titer wells.

Any suitable number and spacing of tip channels may be used with correspondingly sized supply wells and correspondingly arranged and sized titer wells. With a rectangular layout of titer wells, 2, 4, 6 or more legs with channels could be used, with the legs arranged in a corresponding rectangular array. Or optimum speed and accuracy, tips with four channels are preferred, since four will be faster than two and four will fit into supply wells of reasonable size, where six or more will require much larger supply well cross sectional area. If desired, patterns other than rectangular may be used, such as hexagonal or circular patterns. However, for convenience and accuracy a rectangular pattern is preferred.

BRIEF DESCRIPTION OF THE DRAWING

Details of the invention, and of preferred embodiments thereof, will be further understood upon reference to the drawing, wherein:

FIG. 1 is a perspective view of a pipette tip storage rack and one of the pipette tips of this invention;

FIG. 2 is a perspective view of a supply plate having plural supply wells, with a pipette tip in the tip filling position;

FIG. 3 is a perspective view of a microtiter plate with a pipette tip in dispensing position;

FIG. 4 is an elevation view of a pipette and pipette tip with two legs;

FIG. 5 is an end view of a pipette tip, taken on line 5—5 in FIG. 4;

FIG. 6 is an end view similar to that of FIG. 5, showing a pipette tip with four legs and channels;

DETAILED DESCRIPTION OF PREFERRED EMBODIMENTS

Referring to FIG. 1, there is seen a storage rack 10 having a plurality of holes 12 each sized to hold a pipette tip 14 of predetermined configuration, generally a tapered cylinder configured to fit a standard pipette end.

Pipette tip 14 includes a body portion 16 having an opening at first end 18 for slipping over a pipette. A plurality of legs 20 extend from second end 22 of body portion 16. Each leg has a central channel 24 (best seen in FIGS. 5 and 6) which communicates at its proximal end with the body portion 16 interior and has an open distal end sized to dispense a predetermined quantity of liquid relative to other leg channels 24.

A typical supply plate 27 is shown in FIG. 2. Supply plate 27 has a plurality of supply wells 29 containing the liquid to be transported to and dispensed into the titer wells. Each supply well 29 has a cross sectional area sufficient to allow the ends of legs 20 to be inserted well below the surface of liquid in a the well to draw up the required quantity of liquid through channels 24. Preferably, the centers of wells 29 will be spaced in accordance with the spacing of holes 12 in storage plate 10 for convenience in programing automated equipment.

A typical micro titration plate 30 is shown in FIG. 3. In this embodiment, a number (typically 384) of square micro titration wells 32 are formed by a rectangular wall grid. Of course, the wells could be round, rectangular or have other shapes. Typically, plate 30 is formed from a suitable plastic by injection molding and a clear plastic sheet 32 is bonded across the underside of the micro titration plate to form the wells while allowing a person to see by transmitted light what is in the wells. As can be seen, each leg 20 is aligned with one of the wells 32 so that liquid will be dispensed into the correct wells.

It is important that pipette tips 14 be always mounted on a pipette in the same radial orientation so that when the tip is juxtaposed with micro titration wells 32 on a micro titration plate the correct leg and channel 24 will be aligned with the correct micro titration well. To assure the correct orientation, cooperating alignment means are provided on pipette tips 24 and storage rack 10. As seen, each pipette tip 14 preferably has a sideways projecting ridge 26 that fits into a corresponding notch at the edge of each hole 12 in rack 10. In the embodiment shown, the notch is in the plane of the two legs 20. Automated micro titration equipment will bring a pipette into a pipette tip 14, lift the tip out of rack 10, move to a supply well 29, insert the leg channels 24 into the supply liquid, move to the micro titration plate and insert the tip of each leg channel 24 into a different micro titration well and release the liquid. The pipette tip of this invention may be used for transferring liquid between one micro titration plate and another, if desired. The equipment maintains the orientation of the pipette and pipette tip precisely as it was when lifted from rack 12.

If desired, alignment means, such as notches corresponding to notches 28 as seen in FIG. 1 could be provided in supply plate 27 to assure that proper alignment has been maintained.

As can be seen in FIG. 1, legs 20, whether two, four or some other number, are sized and oriented to all fit within one hole. This arrangement will allow all the legs to fit within a correspondingly sized supply well 29 as seen in FIG. 2 for drawing liquid into pipette tip 14. Also, the pipette tip 14 may be used to transfer liquid from wells in one micro titration plate 30 of the sort shown in FIG. 3 to another similar plate.

FIGS. 4–6 show details of preferred embodiments of pipette tip 14. FIGS. 4 and 5 show the pipette tip with two legs 20, each with a central channel 24. Alignment ridge 26 in this embodiment is aligned with the plane of the channels. FIG. 5 illustrates an optimum embodiment in which four legs 20 are arranged in a rectangular array. This arrangement allows use of a reasonably narrow supply well to receive all four legs, while providing sufficient spacing between legs to permit accurate dispensing into a micro titration well arrangement of the sort shown in FIG. 3. Depending on the size of the supply wells and the spacing of the micro titration wells, six or more legs 20 could be used in any suitable pattern, such as hexagonal, rectangular, etc.

While certain specific relationships, materials and other parameters have been detailed in the above description of preferred embodiments, those can be varied, where suitable, with similar results. Other applications, variation and ramifications of the present invention will occur to those skilled in the art upon reading the present disclosure. Those are intended to be included within the scope of this invention as defined in the appended claims.

I claim:

1. A plural channel pipette tip which comprises;

a tubular body for mounting on a single pipette at a first end;

a second end of said tubular body having a plurality of spaced, approximately parallel, legs extending away from said tubular body; and a channel extending through each leg having a proximal end in communication with said tubular body and an open distal end, wherein all of said open distal ends fit within a single supply well, wherein each of said plurality of legs fits within a separate micro titration well in a micro titration place, and wherein at least some of said channels have open distal ends with different cross-sectional areas.

2. A plural channel pipette tip and storage rack system which comprises:

a tubular body for mounting on a single pipette at a first end;

a second end of said tubular body having a plurality of spaced legs extending away from said tubular body;

a channel extending through each leg having a proximal end in communication with said tubular body and an open distal end;

a rack having openings for storing a plurality of said pipette tips prior to use; and cooperating alignment means on said tubular body first end and at said storage rack openings to assure that each pipette tip will mount on each pipette in a predetermined alignment.

3. The plural channel pipette tip and storage rack system according to claim 2, wherein at least some of said channels have open distal ends with different cross-sectional areas.

4. The plural channel pipette tip and storage rack system according to claim 2, wherein said alignment means comprises a ridge on said pipette tip and a cooperating recess in said storage rack at said storage rack openings.

5. The plural channel pipette tip and storage rack system according to claim 2, wherein four of said legs are provided in a rectangular pattern.

6. A kit for performing rapid and accurate titrations which comprises:
- a tubular body for mounting on a single pipette at a first end;
- a second end of said tubular body having a plurality of spaced legs extending away from said tubular body;
- a channel extending through each leg having a proximal end in communication with said tubular body and an open distal end;
- a storage rack having a plurality of holes for simultaneously receiving all of said plural legs on one pipette tip and at least a portion of said tubular body;
- cooperating alignment means on said tubular body and said storage rack to assure that each pipette tip will mount on each pipette in a predetermined alignment;
- a pipette for insertion into said pipette tip and for releasably retaining said pipette tip thereon;
- a supply rack having a plurality of supply wells, each of said wells configured to admit all of said plural legs; and
- a micro-titration plate having a plurality of micro-titration wells, said microtitration wells configured to admit individual said legs into a corresponding plurality of individual micro-titration wells.

7. The kit according to claim 6, wherein at least some of said channels have open distal ends having different cross-sectional areas.

8. The kit according to claim 6, wherein four approximately parallel legs are provided in a rectangular pattern.

9. The kit according to claim 6, wherein two approximately parallel legs are provided.

10. The kit according to claim 6, wherein said alignment means comprises a ridge on said pipette tip and a cooperating recess in said storage rack.

* * * * *